(12) United States Patent
Carbonari

(10) Patent No.: US 7,611,245 B2
(45) Date of Patent: Nov. 3, 2009

(54) PLACIDO PROJECTOR FOR CORNEAL TOPOGRAPHY SYSTEM

(75) Inventor: Kenneth J. Carbonari, Houston, TX (US)

(73) Assignee: EyeSys Vision, Inc., Houston, TX (US)

( * ) Notice: Subject to any disclaimer, the term of this patent is extended or adjusted under 35 U.S.C. 154(b) by 5 days.

(21) Appl. No.: 11/679,644

(22) Filed: Feb. 27, 2007

(65) Prior Publication Data

US 2008/0204659 A1    Aug. 28, 2008

(51) Int. Cl.
*A61B 3/10*    (2006.01)

(52) U.S. Cl. ..................................... 351/212; 351/221

(58) Field of Classification Search .......... 351/200–246
See application file for complete search history.

(56) References Cited

U.S. PATENT DOCUMENTS

| | | | |
|---|---|---|---|
| 4,995,716 A | * | 2/1991 | Warnicki et al. ............ 351/212 |
| 6,152,565 A | | 11/2000 | Liu et al. |
| 6,315,413 B1 | * | 11/2001 | Shimmick et al. ............ 351/212 |
| 6,547,393 B2 | * | 4/2003 | Ruiz ............................ 351/212 |
| 6,572,230 B2 | * | 6/2003 | Levine ......................... 351/221 |

\* cited by examiner

*Primary Examiner*—Mohammed Hasan
(74) *Attorney, Agent, or Firm*—Chris P. Perque; Gardere Wynne Sewell LLP

(57) ABSTRACT

A placido projector for a corneal topography system includes a substrate having dielectric phosphor. The substrate is configured to be activated by electric current and responsive to emit light. A plurality of opaque, concentric rings are formed on the substrate. When the substrate emits light responsive to the electric current, a placido image is projected. The concentric rings can be formed using silk screening or other techniques. The dielectric phosphor can be micro-encapsulated and deposited onto the substrate. The substrate may be an electro-luminance panel. A protective cover is placed adjacent to the substrate to retain the substrate in a predetermined shape. In one embodiment, the placido projector has a frusto conical shape.

14 Claims, 8 Drawing Sheets

PLACIDO PROJECTOR FOR CORNEAL TOPOGRAPHY SYSTEM

FIELD OF THE INVENTION

The present invention relates generally to corneal topography systems. More specifically, the invention relates to a placido projector for a corneal topography system.

BACKGROUND OF THE INVENTION

Increased use of surgical techniques to correct vision problems has resulted in an increased need for data relating to the topography of the cornea of the eye. Deformations in the cornea of the eye are mainly responsible for vision problems experienced by patients. The shape of the patient's cornea is a significant factor to such eye diseases such as myopia. An eye with a perfect vision has a near spherical cornea so that incident light is diffracted inward towards a focal point within the eye. Variations in the shape of the cornea can result in light not being diffracted into the focal point of the eye thereby producing vision problems for the patient. These eye problems are typically corrected by positioning a lens in front of the eye, which is configured to be able to correct for the deformations in the patient's cornea which are causing the eye problem.

In the past, the correction needed by a particular patient was determined by positioning a series of lenses in front of the patient's eye until their vision improved. However, as analytic techniques and instrumentations have become more sophisticated, mapping of the cornea to obtain the overall contour of the cornea has become more common. Corneal topography data provides a treating physician with information as to the localized radius of curvature of a particular cornea. This allows the treating physician to more accurately select contact lenses and it also greatly aids the treating physician in correcting eye deformations through surgical techniques.

Recently, the use of surgical techniques to correct eye problems such as myopia, have become more common. Techniques such as radial keratotomy and other well known techniques require that the treating physician have detailed information as to the configuration of the patient's cornea. With this information, the treating physician can then cut, abate, or otherwise change the outer surface of the cornea at various locations to alter the overall shape of the cornea to thereby correct the patient's vision. In fact, these techniques have become significantly advanced so that treating physicians are able to correct significant nearsightedness or far-sightedness to near perfect vision. The treating physician needs detailed corneal topography information to perform these surgical techniques and also to fit contact lenses in specific situations. As a consequence, corneal topography systems have been developed which provide detailed information about the topography of the outer surface of a patient's cornea.

Corneal topography systems generally project into the patient's eye a placido image which is an image of a plurality of concentric rings or mires. The image of these rings is reflected off of the patient's cornea and is then captured using a camera. Thus, the camera contains a two-dimensional image of the rings being reflected off of the patient's three-dimensional cornea. The position of the reflected rings in the captured image can then be used to calculate the curvature of the patient's eye.

Specifically, it is assumed that a cornea having perfect vision will be generally uniformly spherical. If the placido image was reflected off of a perfectly spherical surface, the reflected rings would appear on a two-dimensional image as a plurality of concentric rings with the two-dimensional location of the rings being related to the curvature of the spherical surface. If, however, the patient's cornea is not perfectly spherical, the positions of the plurality of rings in the resulting reflected image are generally displaced from the corresponding position of the rings that is reflected off of the perfect sphere. A comparison of the position between the image reflected off of the patient's cornea and a corresponding perfect sphere will permit the determination of the deviation of the patient's cornea from a perfect sphere. In this manner, the radius of curvature of the patient's cornea at locations over the entire surface area of the patient's eye can be calculated thereby providing the topography of the patient's cornea.

A placido projector is typically used to project a placido image. The placido projector was first used in 1880 by a Portuguese ophthalmologist named Antonio Placido who used a painted disk (Placido's disk) of alternating black and white rings to project contour lines onto the cornea. Conventional placido projectors comprise a cone of translucent material. The inner surface of the placido projector is coated with a plurality of concentric opaque rings. FIG. 1 shows a placido projector made of a translucent material, such as plastic, which has a plurality of concentric rings painted on its inner surface. FIG. 2 shows the outer surface of the placido projector that is generally frusto conical in shape. A light source such as an EL panel is positioned immediately adjacent to the outer surface of the placido projector so as to uniformly illuminate the placido projector to thereby produce the placido image that is to be reflected off of the patient's cornea.

FIGS. 3 and 4 illustrate the configuration of the light source. The light source is comprised of an EL panel 300 that is cut into a half circle that can be folded together to form the frusto conical shape 400 shown in FIG. 4. As discussed before, the outer surface of the placido projector is also frusto conical. Hence the EL 300 panel includes a cut-out 304 that is sized so that when the EL panel 300 is folded into the frusto conical shape 400, an opening 404 is formed. The opening 404 corresponds to an opening of the placido projector to allow the reflected image of the placido to be received by a camera.

Thus, existing placido projectors comprise a cone of translucent material, the inner surface of which is coated with a plurality of concentric opaque rings. A light source is positioned immediately adjacent to the outer surface of the translucent cone to illuminate the placido projector to thereby produce the placido image that is to be reflected off of the patient's cornea.

While concentric ring images on placido projectors can be produced on a machinist lathe, the production requires a significant investment in tooling and fixtures to hold a uniquely shaped part in a conventional machinist tool, and the process is time intensive. Concentric ring images may be produced by molding operations, which also requires a machining process to add and/or remove opaque material. Also, certain non-circular patterns cannot be created using machining or molding operations.

SUMMARY OF THE INVENTION

The invention is directed to a placido projector for a corneal topography system. The placido projector includes a substrate having dielectric phosphor. The substrate is activated by electric current and emits light responsive to the electric current. An opaque pattern is formed on the substrate. A placido image is projected when the substrate emits light responsive to the electric current. The pattern may be a plurality of concentric rings or any other desired patterns. The pattern may be formed by silk screening or any other process. The substrate may be deposited with micro-encapsulated phosphor. A cover is placed adjacent to the substrate to retain the substrate in a predetermined shape.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
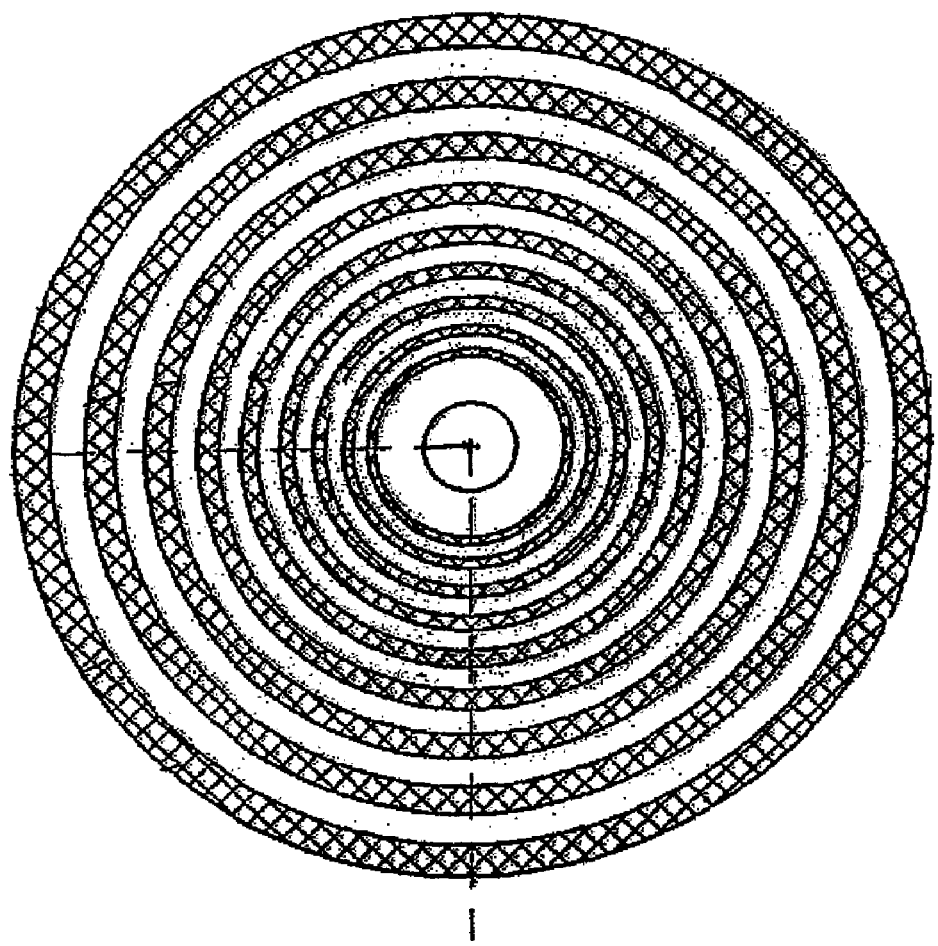
FIG. 1 shows a conventional placido projector made of a translucent material, such as plastic, which has a plurality of concentric rings painted on its inner surface.
Figure 2:
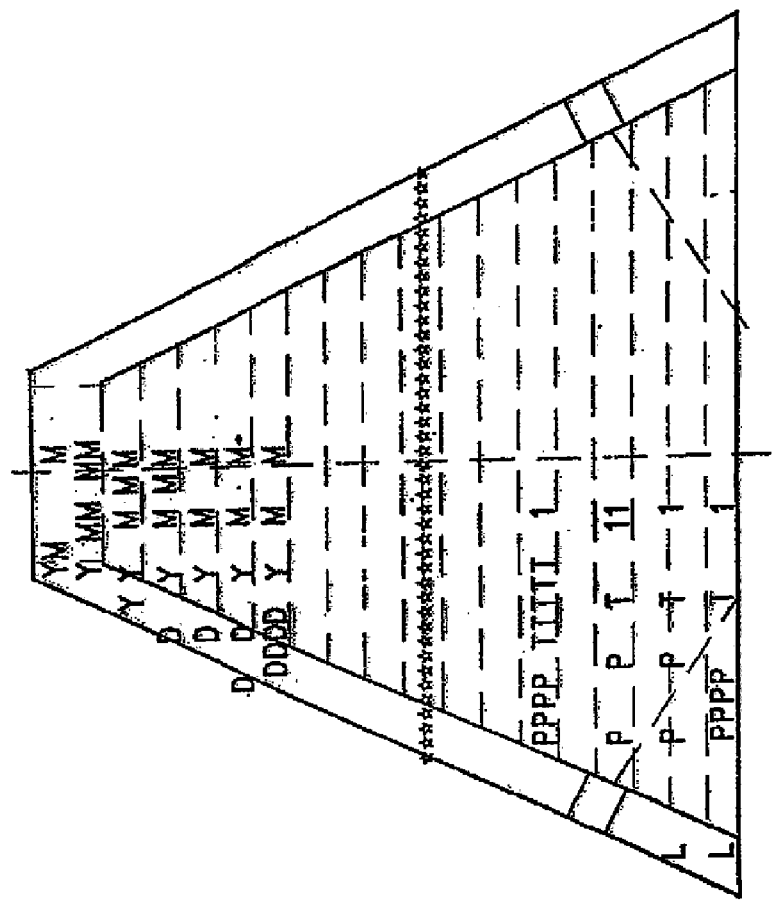
FIG. 2 shows the outer surface of the placido projector that is frusto conical in shape.
Figure 3:
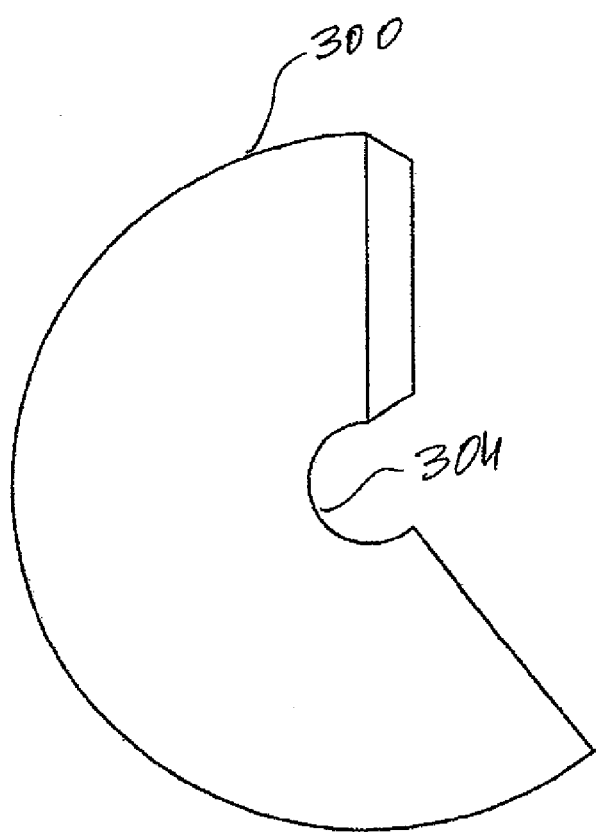
FIGS. 3 and 4 illustrate the configuration of a light source.
Figure 4:
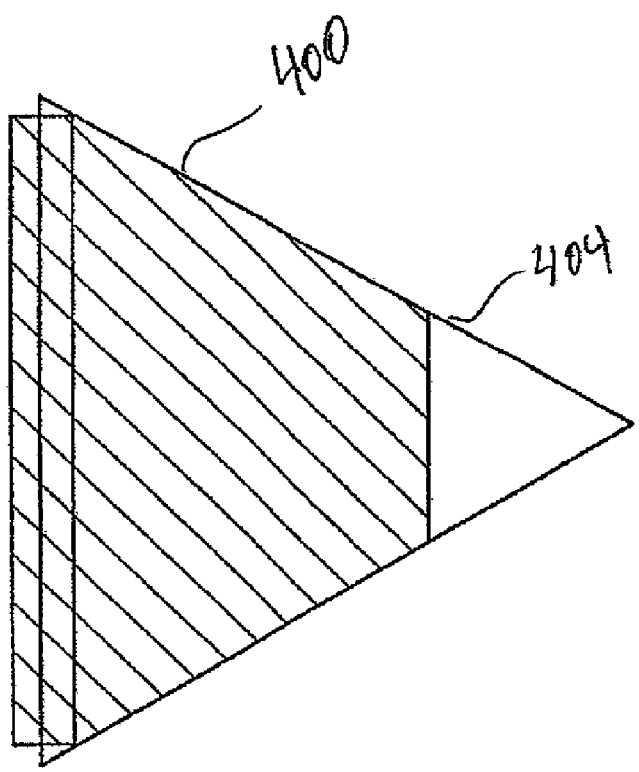
Figure 5:
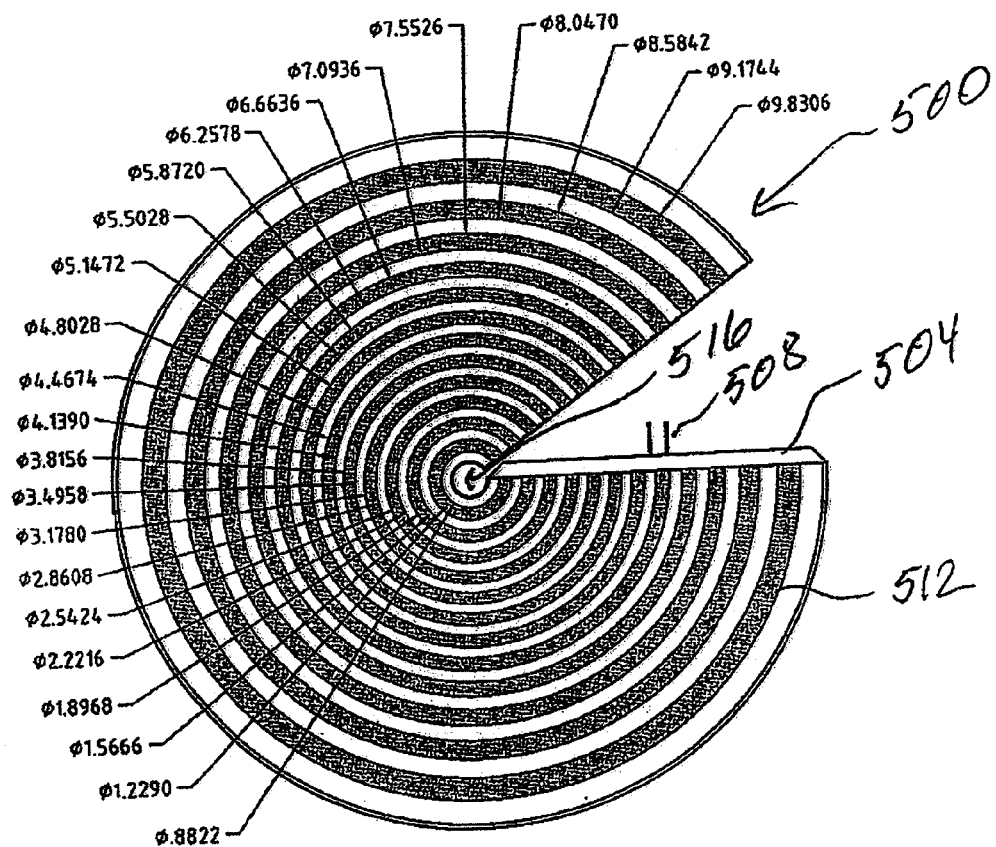
FIG. 5 illustrates a placido projector in accordance with one embodiment of the invention.

FIG. 5 illustrates a placido projector 500 in accordance with one embodiment of the invention. The placido projector comprises a substrate 504. The substrate 504 may be made from a flexible material such as polyester. The substrate 504 is embedded with dielectric phosphor. The substrate 504 is coupled to electric conductors 508 so that electric current can be applied to the substrate 504.

In one embodiment, electric conductors 508 may be printed on the substrate 504 so that the substrate 504 can be electrically excited. When electric current is applied to the substrate 504, the substrate 504 emits light. As will be apparent, the substrate 504 can be an EL panel that emits light when excited with AC current.

One side of the placido projector 500 is coated with a plurality of concentric opaque rings 512. In one embodiment, silk screening method is used to coat one side of the placido projector 500 with a plurality of opaque concentric rings. Silk screening is also known as screen printing by which a negative of a desired pattern is produced on a reusable screen material. A light source (e.g., EL panel) is positioned beneath the screen, and an opaque liquid (e.g., paint) is drawn across the surface applying material to the desired locations on the EL panel. The opaque material blocks the emission of light from the desired locations and thus the intended pattern is reflected from the corneal surface.

In another embodiment, pad printing process may used instead of silk screening. The pad printing process requires a pad, cliché and ink. The cliché is made of a hard polymer or steel material and is configured with the desired design etched into it to act as a reservoir for the ink. The pad, typically made from a silicone rubber, is first pressed against the ink reservoir in the cliché. The pad picks up the design and transfers it by pressing against the object. The properties of silicone allow the ink to stick temporarily to the pad yet be fully released when it comes in contact with the object.

It will become apparent to those skilled in the art that other methods can be used to coat the placido projector with the plurality of concentric rings. Also, while the placido projector 500 is shown to be coated with a plurality of concentric rings, other patterns can be placed on the projector.

Figure 6:
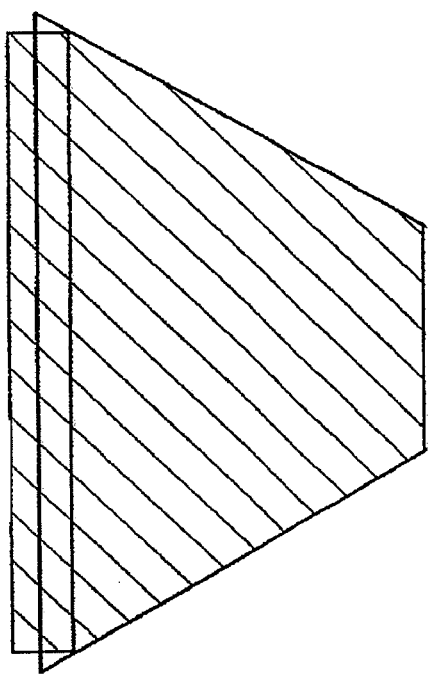
FIG. 6 shows the placido projector of FIG. 5 is folded together to form the frusto conical shape.

As shown in FIG. 5, the placido projector 500 is comprised of a substrate 504 that is cut into a half circle with cut out 516. The cut out 516 is sized so that when the placido projector 500 is folded together to form the frusto conical shape 600 shown in FIG. 6, an opening 604 is formed. The opening 604 allows the reflected image of the placido projector to be received by a camera (not shown in FIG. 6). The inner surface of the placido projector (not shown in FIG. 6) is coated with the plurality of the concentric rings.

In one embodiment, the placido projector is made of a translucent material, such as plastic, which has a plurality of concentric rings painted on its inner surface.

In one embodiment, the placido projector is placed behind a protective cover. The protective cover has a frusto conical shape and is designed to retain the placido projector. The protective cover is made from a transparent plastic to allow the placido image to project forward. The protective cover has an opening that corresponds to the opening of the placido projector. The placido projector can be attached to the protective cover through the use of tape of any other suitable adhesive.

The placido projector 600 is frusto conical shaped wherein the inner surface of the placido projector is coated with a plurality of concentric rings. When the placido projector is excited by AC current, the placido projector illuminates so that an image of a plurality of concentric rings is projected out of the cavity. The inner end of the placido projector includes the opening. The opening receives a reflected image of the plurality of the rings reflected off of the patient's cornea. A camera (not shown) is positioned behind the opening to capture the reflected image. The camera transforms the reflected image into an electronic signal indicative of the reflected image from the patient's cornea. The electronic signal is provided to an image analyzer coupled to the camera. The image analyzer analyzes the signal to determine the corneal topography of the patient's cornea.

Figure 7:
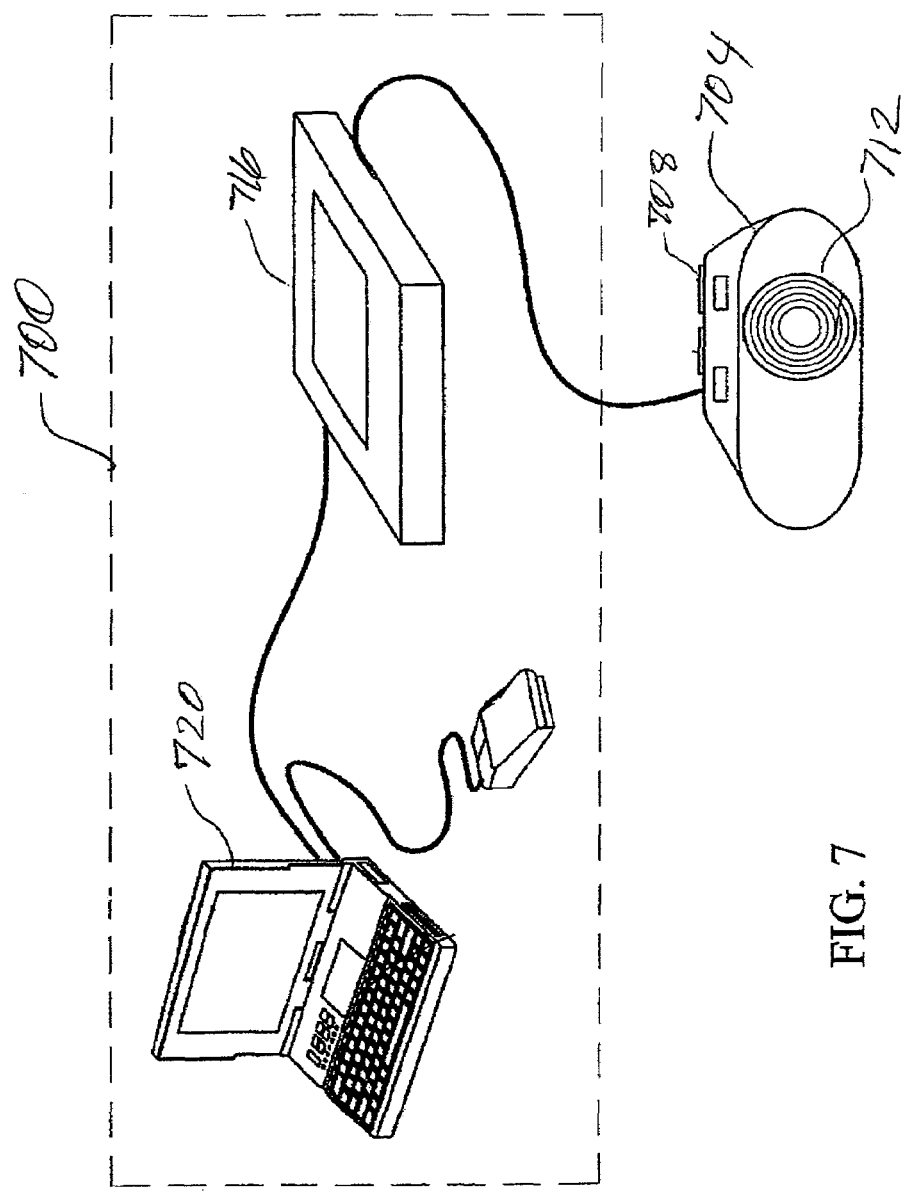
FIG. 7 shows a corneal topography system in accordance with one embodiment of the invention.

FIG. 7 shows a corneal topography system 700 in accordance with one embodiment of the invention. The system 700 includes a projector assembly 704 incorporating a camera 708 and a placido projector 712. An image analyzer 716 is coupled to the camera 708. The image analyzer 716 is adapted to receive a signal indicative of the placido image reflected from the patient's cornea and is configured to determine the corneal topography of the patient from the signal. The image analyzer may be coupled to a personal computer 720 to display the results.

The present invention offers various advantages over existing placido projectors. The invention allows various patterns to be created that would not have been otherwise possible. For example, patterns can be created by a graphic software computer application and then applied to a light source directly using a laser or an ink jet printer. In addition to printing directly on a light source, various patterns or printing techniques can be applied to other media such as transparencies or transparent/translucent thin films.

Figure 8:
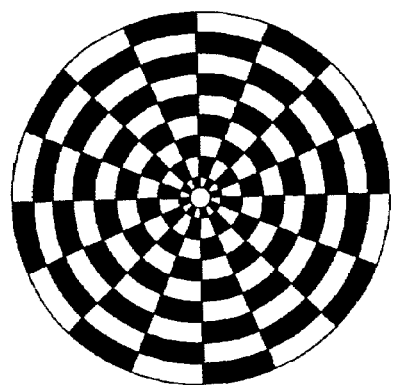
FIGS. 8-10 show placido projectors having various other patterns in accordance with other embodiments of the invention.
Figure 9:
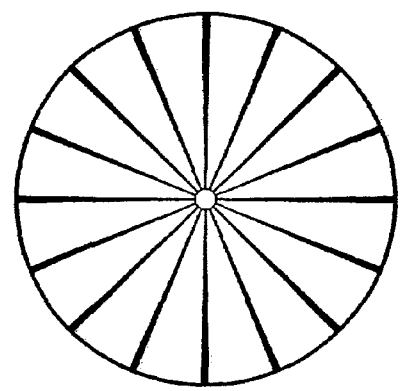
Figure 10:
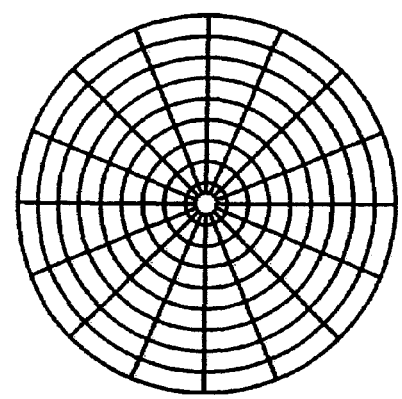

FIGS. 8-10 show various other patterns created using the present invention. FIG. 8 shows a placido projector having a checker board pattern in accordance with one embodiment of the invention. FIG. 9 shows a placido projector having radial lines in accordance with one embodiment of the invention. FIG. 10 shows a placido projector having a combination of radial lines and a checker board pattern in accordance with one embodiment of the invention.

While the structures, apparatus and methods of this invention have been described in terms of preferred embodiments, it will be apparent to those of skill in the art that variations may be applied to the structures, apparatus and/or methods and in the steps or in the sequence of steps of the method described herein without departing from the concept, spirit and scope of the invention. All such substitutes and modifications apparent to those skilled in the art are deemed to be within the spirit, scope and concept of the invention as defined by the appended claims.

What is claimed is:

1. A frusto-conical shaped placido projector for a corneal topography system, comprising:
   an electroluminance panel having a substrate having dielectric phosphor, the substrate configured to be activated by electric current and responsive to emit light, the substrate being deposited with micro-encapsulated phosphor;
   a plurality of opaque concentric rings formed on the substrate; and
   a frusto-conical shaped cover configured to retain the substrate in a frusto-conical shape, wherein a placido image is projected when the substrate emits light responsive to the electric current.

2. The frusto-conical shaped placido projector of claim 1, wherein the opaque concentric rings are formed on the substrate by silk screening.

3. A corneal topography system comprising:
   a projector assembly incorporating a camera and a placido projector, wherein the placido projector projects a placido image when activated by electric current and wherein the camera obtains an image of the placido image reflected from a patient's cornea;
   an image analyzer coupled to the camera, the image analyzer adapted to receive a signal indicative of the placido image reflected from the patient's cornea and configured to determine the corneal topography of the patient from the signal, wherein the placido projector comprises:
      an electroluminance panel having a substrate having dielectric phosphor, the substrate being deposited with micro-encapsulated phosphor; and
      a plurality of opaque concentric rings formed on the substrate.

4. The corneal topography system of claim 3, wherein the reflected signal is indicative of the corneal topography of the patients cornea.

5. The placido projector of claim 3, wherein the opaque pattern is formed on the substrate by silk screening.

6. The placido projector of claim 3, wherein the substrate is activated by alternating current (AC).

7. A placido projector for a corneal topography system, comprising:
   a flexible electroluminance panel having a substrate having dielectric phosphor, the substrate being deposited with micro-encapsulated phosphor;
   one or more electric conductors coupled to the substrate to activate the substrate by electric current, the substrate responsive to emit light when activated by electric current; and
   a plurality of opaque concentric circles formed on one side of the substrate, wherein a placido image is projected when the substrate emits light responsive to the electric current.

8. The placido projector of claim 7, wherein the flexible substrate has a frusto-conical shape.

9. The placido projector of claim 8, wherein the opaque concentric rings are formed on the substrate by silk screening.

10. A method of projecting a placido image for a corneal topography system comprising:
    activating, by electric current, an electroluminance panel having a substrate having micro-encapsulated dielectric phosphor, the substrate having a plurality of opaque concentric rings formed thereon, the substrate emitting light responsive the electric current, wherein a placido image is projected when the substrate emits light responsive to the electric current.

11. The method of claim 10, wherein the plurality of concentric rings is formed on one side of the substrate.

12. The method of claim 10, wherein the opaque concentric rings are formed on the substrate by silk screening.

13. The method of claim 10, wherein the substrate is folded into a frusto conical shape.

14. A method of obtaining corneal topography information comprising:
    positioning a placido projector adjacent to a patient's cornea;
    projecting a placido image by the placido projector;
    sensing with a camera a reflected placido image from the patient's cornea, wherein the reflected placido image is indicative of the patient's corneal topography, wherein the placido projector comprises:
       an electroluminance panel having a substrate having micro-encapsulated dielectric phosphor, the substrate configured to be activated by electric current and responsive to emit light;
       a plurality of concentric rings formed on the substrate, wherein the placido image is projected when the substrate emits light responsive to the electric current.

* * * * *